United States Patent [19]

Linden et al.

[11] Patent Number: 5,634,936
[45] Date of Patent: Jun. 3, 1997

[54] DEVICE FOR CLOSING A SEPTAL DEFECT

[75] Inventors: Bradley Linden, Eden Prairie; Donald F. Palme, II, Dayton; Paul J. Buscemi, Long Lake; Thomas J. Holman, Minneapolis, all of Minn.

[73] Assignee: Scimed Life Systems, Inc., Maple Grove, Minn.

[21] Appl. No.: 383,824

[22] Filed: Feb. 6, 1995

[51] Int. Cl.$^6$ ............................................. A61B 17/08
[52] U.S. Cl. .................. 606/213; 606/215; 606/153; 606/191; 604/60
[58] Field of Search .......................... 606/213, 215, 606/153, 191; 604/15, 60, 93, 101, 53, 919

[56] References Cited

U.S. PATENT DOCUMENTS

| | | |
|---|---|---|
| 3,704,711 | 12/1972 | Park . |
| 3,848,602 | 11/1974 | Gutnick . |
| 3,874,388 | 4/1975 | King et al. . |
| 3,952,742 | 4/1976 | Taylor . |
| 4,000,743 | 1/1977 | Weaver . |
| 4,090,518 | 5/1978 | Elam . |
| 4,180,076 | 12/1979 | Betancourt . |
| 4,198,981 | 4/1980 | Sinnreich . |
| 4,292,976 | 10/1981 | Banka . |
| 4,327,736 | 5/1982 | Inoue . |
| 4,329,993 | 5/1982 | Lieber et al. . |
| 4,351,342 | 9/1982 | Wiita et al. . |
| 4,484,579 | 11/1984 | Meno et al. . |
| 4,672,969 | 6/1987 | Dew . |
| 4,836,204 | 6/1989 | Landymore et al. . |
| 4,854,320 | 8/1989 | Dew et al. . |
| 4,860,745 | 8/1989 | Farin et al. . |
| 4,917,089 | 4/1990 | Sideris . |
| 4,985,029 | 1/1991 | Hoshino . |
| 4,997,431 | 3/1991 | Isner et al. . |
| 5,071,417 | 12/1991 | Sinofsky . |
| 5,108,420 | 4/1992 | Marks . |
| 5,139,480 | 8/1992 | Hickle et al. . |
| 5,171,259 | 12/1992 | Inoue . |
| 5,192,301 | 3/1993 | Kamiya et al. . |
| 5,258,020 | 11/1993 | Froix . |
| 5,258,042 | 11/1993 | Mehta . |
| 5,391,183 | 2/1995 | Janzen et al. ................ 606/215 |
| 5,486,195 | 1/1996 | Myers et al. ................. 606/215 |

FOREIGN PATENT DOCUMENTS

| | | |
|---|---|---|
| 0 541 063 A2 | 5/1993 | European Pat. Off. . |
| 0 545 091 | 6/1993 | European Pat. Off. . |
| 93/16738 | 9/1993 | European Pat. Off. ........ 606/214 |
| 676285 | 7/1979 | U.S.S.R. . |
| 952234 | 8/1982 | U.S.S.R. . |
| 1531995 A1 | 12/1989 | U.S.S.R. . |
| 1 509 023 | 4/1978 | United Kingdom . |
| WO93/13712 | 7/1993 | WIPO . |

OTHER PUBLICATIONS

"Permanent Inflation of Detachable Balloons with a Low-Viscosity, Hydrophilic Polymerizing System[1]", *Radiology*, vol. 169, No. 3, (Dec. 1988), pp. 787-790, by Katsuya Goto, MD et al.

*Progress In Biomedical Optics*, "Proceedings of Lasers in Dermatology and Tissue Wedding", By Oon T. Tan, M.D. et al., dated Jan. 21-22, 1991, SPIE vol. 1422, Session 2, pp. 97-157.

*Primary Examiner*—Michael Buiz
*Assistant Examiner*—Mark S. Leonardo
*Attorney, Agent, or Firm*—Vidas, Arrett & Steinkraus

[57] ABSTRACT

A device for closing off a septal defect including a polymeric self-hardening material in a specific conformation which is delivered by a catheter device to the area of defect either directly on the cardiac tissue or into a balloon which spans both surfaces of the defect, and hardened in-situ by change in pH or ionic concentration, organic solvents, by permeation of a secondary material capable of precipitation, or by exposure to heat, light or laser energy. In blood, the device may be hardened through photopolymerization or a cooperative effect of coagulation, precipitation or ionization. The device can be made of biodegradable material impregnated with growth factors, mitogenic factors or other determinants which can improve tissue growth such that tissue ingrowth can occur over a period of time. The catheter itself may be an ultrasonic imaging catheter.

46 Claims, 8 Drawing Sheets

DEVICE FOR CLOSING A SEPTAL DEFECT

BACKGROUND OF THE INVENTION

1. Field of the Invention

The present invention relates generally to the closure of intravascular defects and more specifically to a device for closing a cardiovascular or cardiac septal defect, the device being made of a polymeric material delivered to the site of the defect by a catheter and hardened in-situ to a predetermined configuration to function as a plug.

2. General Background

The normal heart is divided into four chambers, the two upper being the left and right atria and the two lower being the left and right ventricles. The atria are separated from each other by a muscular and a membranous wall, the interatrial septum, and the ventricles by the interventricular septum.

Either congenitally or by acquisition, abnormal openings, holes or shunts can occur between the chambers of the heart or the great vessels (interatrial and interventricular septal defects or patent ductus arteriosus and aortico-pulmonary window respectively), causing shunting of blood through the opening. The deformity is usually congenital, resulting from a failure of completion of the formation of the septum, or wall, between the two sides during fetal life when the heart forms from a folded tube into a four-chambered, two unit system.

These deformities can carry significant sequelae. For example, with an atrial septal defect, blood is shunted from the left atrium of the heart to the right, producing an overload of the right heart. In addition to left-to-right shunts such as occur in patent ductus arteriosus from the aorta to the pulmonary artery, the left side of the heart has to work harder because some of the blood which it pumps will recirculate through the lungs instead of going out to the rest of the body. The ill effects of these lesions usually cause added strain on the heart as well as the lungs which ultimately causes failure of the lungs and/or heart.

Previously, intracardiac septal defects and extracardiac pathologic vascular communications have required surgical intervention. To date the most common method of closing intracardiac shunts, such as atrial-septal defects and ventricular-septal defects, involves an intracardiac (open heart) operation requiring a sternotomy or a thoracotomy and diversion of the blood from the heart with the use of a cardiopulmonary bypass. The heart is then opened, the defect is sewn shut by direct suturing with or without a patch of synthetic material (usually of Dacron, teflon, silk, nylon or pericardium), and the heart is closed. The patient is then taken off the cardiopulmonary bypass machine, and the chest closed.

In place of direct suturing, closures of interauricular septal defects by means of a prosthesis have been disclosed. U.S. Pat. No. 3,874,388 discloses a shunt defect closure system including a pair of opposed umbrella-like elements locked together in a face to face relationship and delivered by means of a catheter, whereby a defect is closed. U.S. Pat. No. 4,836,204 discloses a double-balloon septal defect occlusion catheter used in conjunction with a surgical procedure to temporarily close septal perforations, particularly spontaneous ventricular septal perforations following acute myocardial infarction.

U.S. Pat. No. 5,192,301 discloses a deformable plug of a shape memory polymer of polynorbornene, styrene-butadiene copolymer, polyurethane, or transisoprene having a recovery temperature of 20° C.–70° C., and a device for closing a septal defect including the plug, a catheter and a guide wire. The plug has a flange on at least one side of the defect and is retained in the body as a "rubbery, flexible member".

There still exists a need, however, for a simple method of closing septal defects, either temporarily or permanently, with an improved plug made of a bioabsorbable material that is hardened in-situ.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. § 1.56(a) exists.

SUMMARY OF THE INVENTION

The present invention provides devices and method for closing off or plugging a septal defect, the devices being made of hardenable polymeric materials in specific conformations which are delivered to the area of defect by a catheter means and hardened in-situ by change in pH or ionic concentration, organic solvents, by permeation of a secondary material capable of precipitation, or by exposure to heat or light. The polymeric material may also be hardened by means of laser energy or by any other suitable means. In blood, one form of the device may be hardened through a cooperative effect of coagulation, precipitation or ionization. The device can be made of biodegradable material impregnated with growth factors, mitogenic factors or other determinants which can improve tissue growth such that tissue ingrowth can occur over a period of time. The delivery catheter itself, which is preferably used to position and install devices of this invention, may be an ultrasonic imaging catheter, which may optionally be controlled from the exterior.

The device may be introduced into the area of a septal defect either directly on the cardiac tissue or inside a balloon or mesh and can be made of tissue compatible material which promotes tissue ingrowth or covering. The injectable material or the material of the balloon or mesh itself may or may not be biodegradable depending on the specific application.

The device may contact both sides of the septum thereby plugging the septal defect. The polymeric material of the device may be in the form of a sleeve delivered to the site of the defect by means of an inflatable balloon over which the sleeve is placed prior to delivery. The balloon is removed after delivery, shaping and either partial or complete hardening of the sleeve.

The septal defect closure device of the present invention may be used to close the ductus arteriosus (The prenatal canal between the pulmonary artery and the aortic arch which normally closes soon after birth), an atrial septal defect, or ventricular septal defect, a defect in the wall of the bladder, bowel, stomach, esophagus, tracheobronchial tree or cerebral ventricular system. The device may also be used to block or fill an artery, vein, ureter, lymphatic vessel, branch of the tracheobronchial tree, or any other vessel-like structure.

The device may be compressible and may be in any shape which is suitable for filling and plugging a defect. A dumbbell shape may be suitable for some septal defects, but the device may also take the shape of a defect itself when the defect is not uniform in shape or if the device is applied in a vessel such as the ductus. In such a case the device is suitably deformable or flexible. The device may be formed of a solid film or of a woven mesh. The defect may be contacted by the surface of the polymeric material, or by a balloon filled with the material, the balloon optionally being mitogenic and/or bioabsorbable. Where the device is a mesh, the mesh will be attached by hardening and/or adhesion about the periphery of the defect.

DETAILED DESCRIPTION OF THE INVENTION

The present invention is a device for closing off or plugging a septal defect. The device may be provided in a variety of embodiments. In one embodiment, a polymeric self-hardening material is introduced into the area of a septal defect. The hardenable material may be provided and used by itself to be placed directly on the cardiac tissue or it may be included within a balloon. The device may span both sides of the septal defect. In another embodiment, the device may comprise a plug-like body of hardenable foam, gum or sponge-like material. In yet another embodiment, it may take the form of a sleeve which is formed to a hardened plug-like configuration by means of a delivery balloon. The sleeve may be of a foam or sponge-like material, or alternatively, the sleeve may be a mesh expanded by the balloon to span the defect, providing a framework for gradual cellular growth to fill the defect. In still another embodiment, if may take the form of a filled balloon which functions as a plug.

The balloon in some embodiments serves only as a delivery device while in other embodiments, it is a part of the plug-like configuration which remains in the defect. In these embodiments, the material and the balloon can be made of biodegradable material such that tissue ingrowth can occur over a period of time both into the balloon itself followed by growth into the filling material, or directly into the filling material if there is no balloon. The balloon and/or the filling material may be mixed with impregnated chemotactic or growth factors, collagen gel, collagen fibrils, mitogenic factors or other determinants which can alter the reaction of the surrounding tissue and improve tissue growth.

The filling material may or may not be a polymer. The filling material may be either a polyurethane foam formed from the mixture of isocyanates and polyols, a latex material or a polymer formed from a free radical reaction with a secondary catalyst added after the polymer. The polymeric material may be altered by heating, cooling or exposure to light which may cause it to solidify. The polymeric material may be hardened by means of laser energy.

The polymer may be a polyphosphazine with active chlorine groups that react with hydroxy groups upon contact with water and with amine groups. Thus polyphosphazines that are protected from air or moisture in the balloon, or are in solution to be injected into the balloon are followed by an aqueous solution. The amine or hydroxyl content of the polymer would depend on the pre-reacted portion of the chlorine on the backbone of the polyphosphazine.

The device may alternatively be formed from mixtures of methyl methacrylate 70% by weight, and burlymethacrylate 29% by weight and AIBN initiator, which would be hardened by exposure to either light, heat or laser energy.

The polymer from which the device is made may also be formed from polyisocyanates and amines or hydroxyl groups. Polyisocyanates and amines or hydroxyls also form chemical bonds when mixed in equal molar ratios. Mixtures of polyethylene glycol 25 mole %, and/or aliphatic diamines 25 mole % in equal molar proportions to the free isocyanates as methylene diisocyanate 50 mole % and less than about 0.2% by weight of dibutyl tin dilaurate catalyst are mixed quickly and uniformly in the process of injection into the balloon. Depending on the ratio of the aliphatic portion and the glycol portion, a more or less rubbery plug will be formed.

Other more slowly crosslinking reagents such as aldehydes added in excess to proteins such as collagen may be used as well.

The delivery means may be a catheter which is typically comprised of a delivery lumen for the polymeric material or sleeve, a lumen for a guide wire, and a lumen for an ultrasonic visualization probe. Other types of delivery catheters will be useable also.

One application of such a device could be as an intravascular stent. The stent would be folded onto a balloon, hardened by an increase or decrease in pH or ionic concentration or an organic solution, softened by the same methods essentially in reverse, expanded and then essentially hardened into place by a second reversal of the modulus change procedure.

The stent or sleeve must first have some hardened consistency to push out of the delivery catheter. It must then be softened to expand, then harden in place. It may be possible to pull out a soft material, kept soft by a flow of liquid in the catheter, and once it comes in contact with blood and the flow from the catheter ceases, to harden in place. In this second scenario, the material need not be hardened first.

Figures 1, 2:
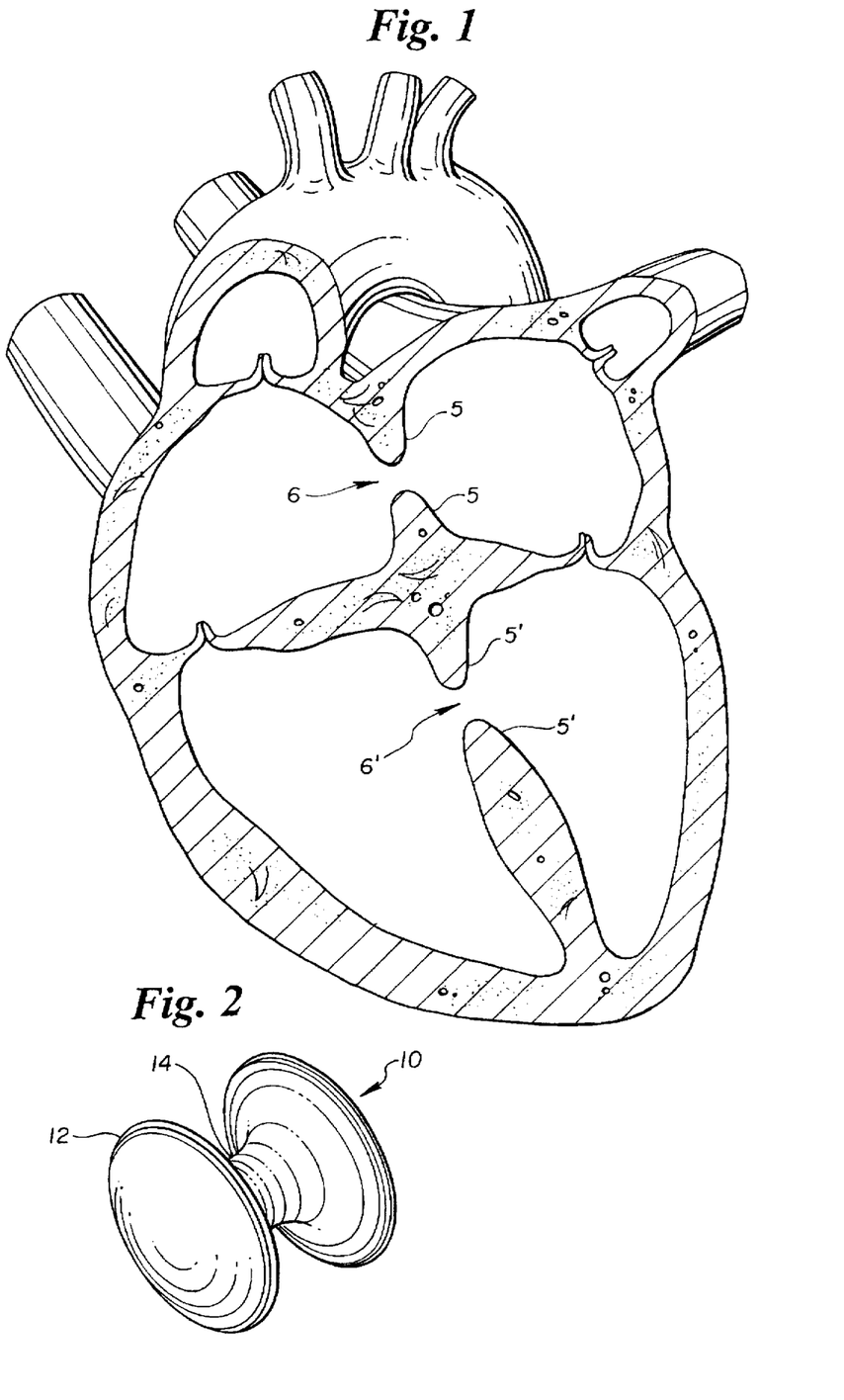
FIG. 1 shows a sectional view of a human heart, showing a typical atrial septal defect (ASD) and a typical ventricular septal defect (VSD) prior to closure according to the present invention.
FIG. 2 shows a perspective view of a septal defect closure device of the present invention.

Referring now to the Figures, FIG. 1 is a sectional view of a human heart showing defects in septal tissue 5,5', a typical atrial septal defect (ASD) 6', and a typical ventricular septal defect (VSD) 6', prior to closure. The defects are shown together for illustrative purposes only, not as a depiction of multiple septal defects. However, multiple defects may be present.

Figure 4A:
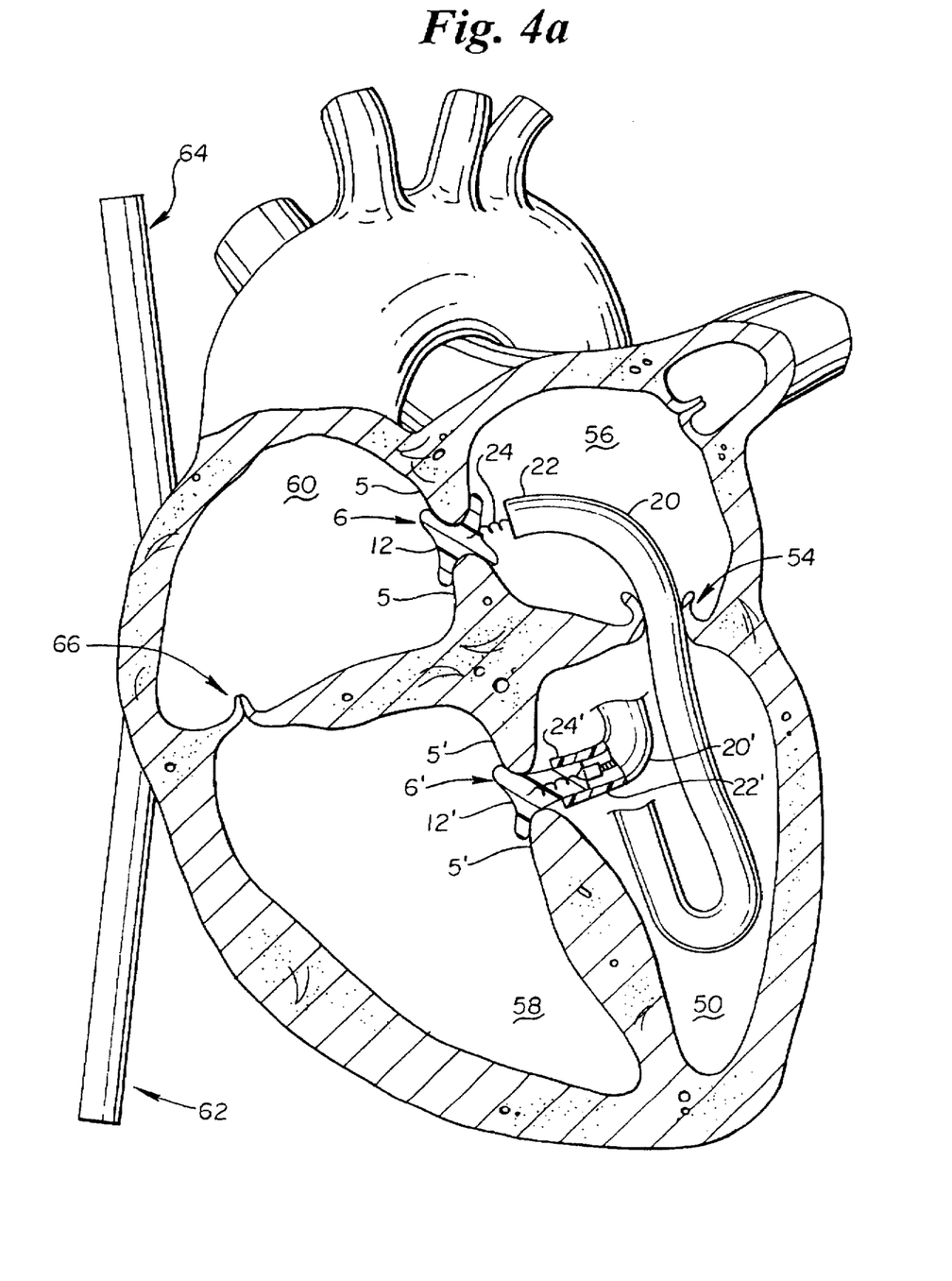
FIGS. 4a and 4b are anterior to posterior sectional views showing the delivery and placement of the septal defect closure device of FIG. 2.
Figure 4B:
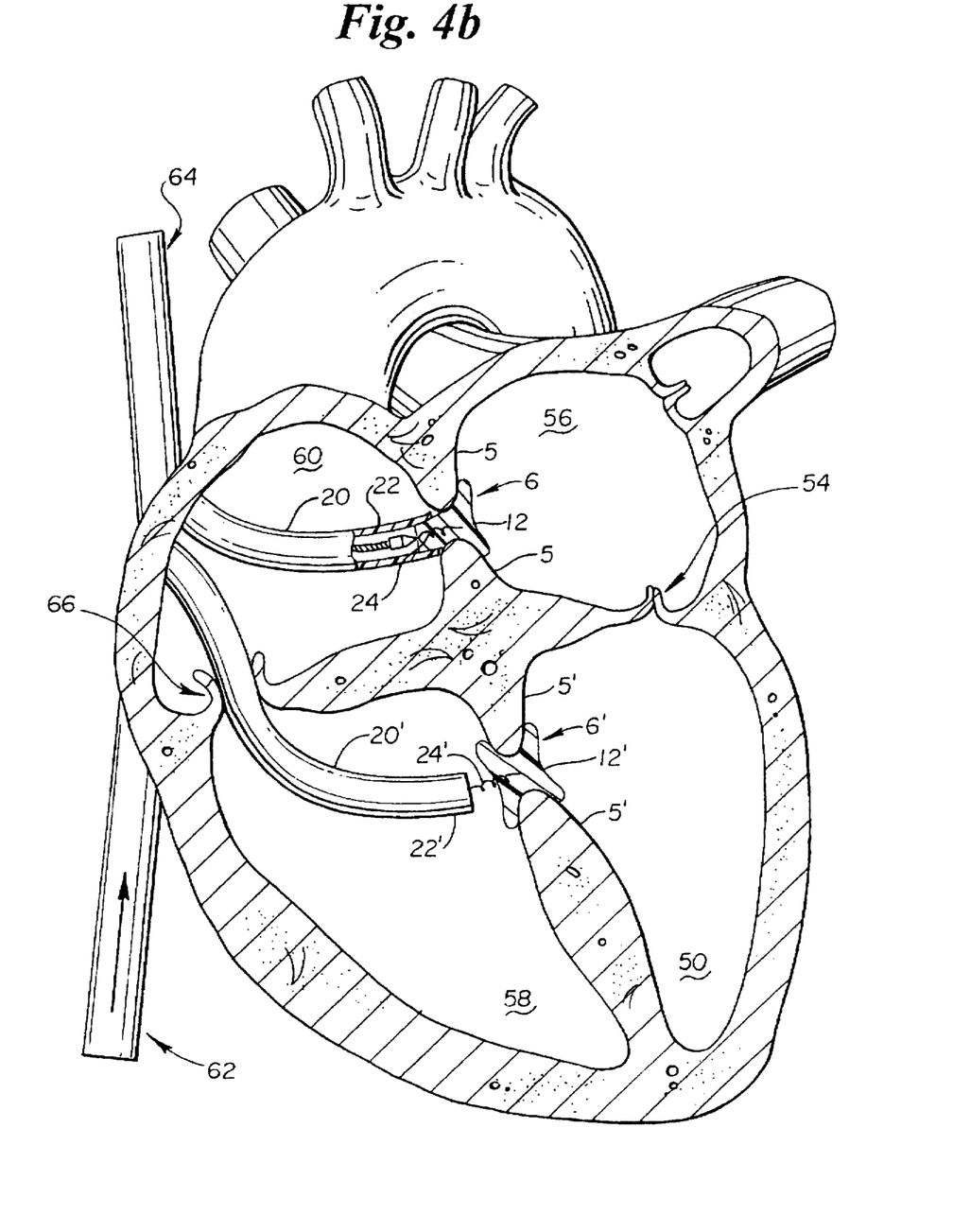
Figure 5:
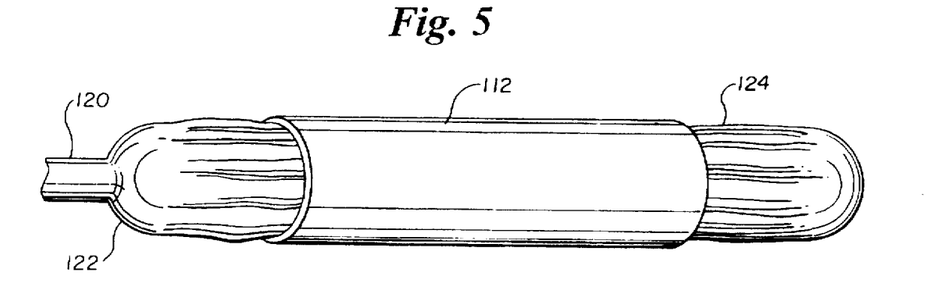
FIG. 5 is a perspective view of an alternative embodiment of the septal defect closure device comprising an expandable closure sleeve and an expansion balloon.
Figure 7:
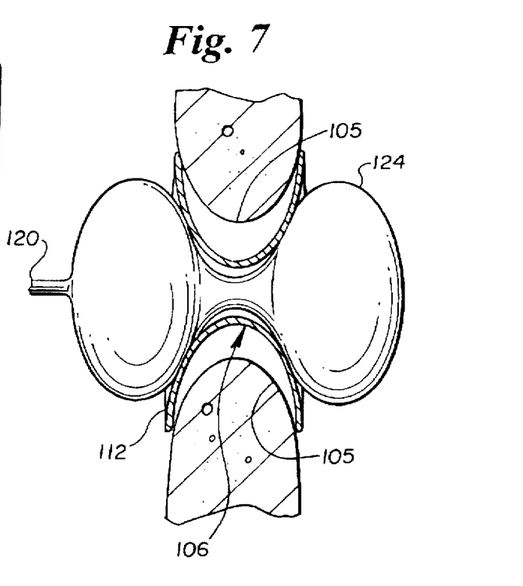
FIG. 7 is a fragmentary sectional view thereof showing the expansion balloon and the expanded closure sleeve in place in the septal defect.
Figure 8:
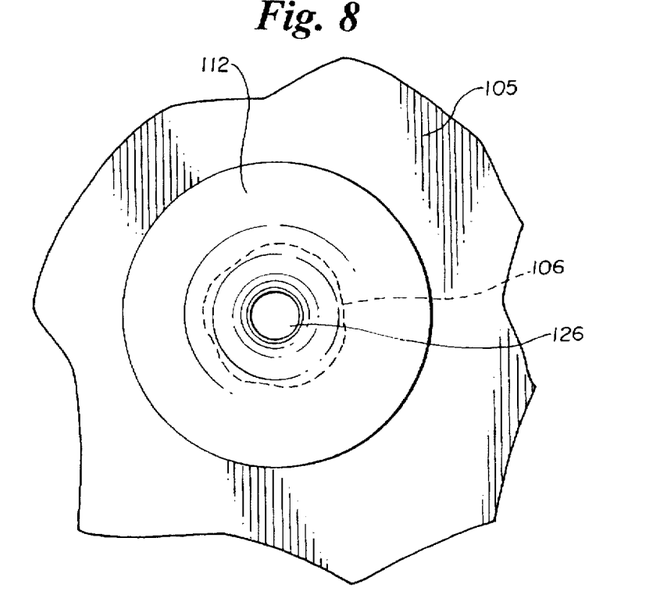
FIG. 8 is a fragmentary view showing the expanded closure sleeve in place in the septal defect after the removal of the expansion balloon.
Figure 9:
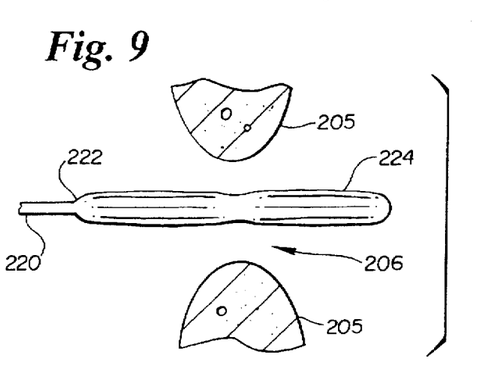
FIGS. 9, 10 and 11 are fragmentary views showing the installation of an alternative embodiment of the septal defect closure device, the device comprising an expansion balloon inflated with a polymeric expansion fluid.
Figure 10:
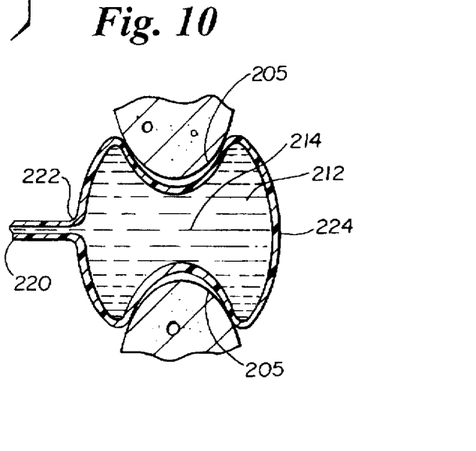
Figure 11:
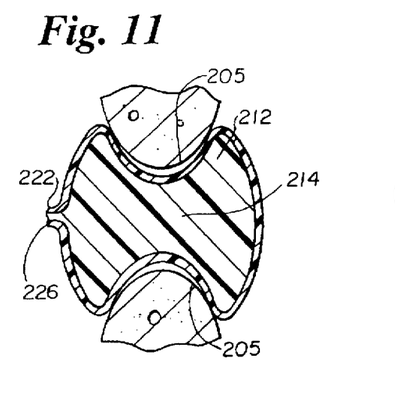

As shown in FIG. 2, a device of the invention shown generally at 10 in one embodiment, is a preshaped plug 12 in the form of a disc with a narrower center portion 14. In this form, the device 10 serves as a plug 12 which is inserted into a tissue defect such as a septal defect. The polymeric material in this embodiment is ideally a polymeric self-hardening foam or sponge material which is soft and easily deformable so that it can be readily plugged into the defect. The plug 12 is introduced into the area of a septal defect either directly on the cardiac tissue as shown in FIGS. 4, 7 and 8, or into a balloon which spans both surfaces of the defect and contacts both sides of the septum, as shown in FIGS. 9–11.

Figure 3:
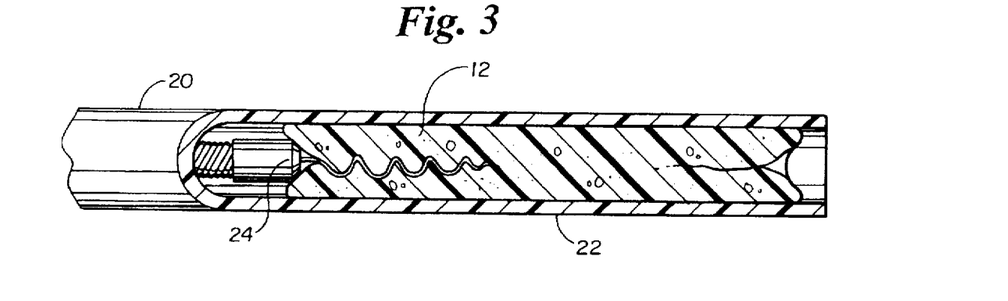
FIG. 3 is a fragmentary view of the device of FIG. 2 inserted into a delivery catheter, the catheter having a portion cut away.

The plug 12 is made of a polymeric material in a specific conformation which reacts with a hardening agent after being installed in the septal defect to change the modulus of the material but not the preformed shape. As the material hardens, its modulus increases. In its original physical form, the material is compliant and able to be folded, compressed or the like. This malleability allows the plug 12 to be inserted into a tube or catheter for delivery to an area of defect. FIG. 3 shows the plug 12 in compressed deliverable form within a delivery tube or catheter 20. The plug 12 is compressed, and held in catheter 20 at its distal end 22 by means of a corkscrew holder 24. Alternatively, the catheter 20 and plug 12 may be releasably connected by a threaded bore (not shown) located in the plug 12 and a threaded protrusion (not shown) at distal end 22 of catheter 20.

The polymer may consist of a polymeric backbone containing hydroxyl, carboxylic or amine side groups which may be reacted with low molecular weight, i.e. 200–1000 MW, diisocyanates. The low molecular weight polymers would serve to chemically crosslink the higher molecular weight polymer which carries the first reactive sidechains. Polyphosphazines which contain residual chloride side chains would react with hydroxyl containing polymers so that polyphosphazine with such side chains would crosslink with polyvinyl alcohol.

Alternatively, the side chains may have terminal acid groups as carboxylic or gamma-carboxylic acids, which can chelate calcium ions. If the chelating groups were first saturated with sodium ions or other monovalent ions prior and during delivery, and subsequently permeated with calcium or other divalent ions at the time of hardening, the backbone would be ionically crosslinked. If the polymer backbone contained double bonds as in polybutadiene with or without lower molecular weight polymers containing double bonds as acrylic acids, and these polymers were exposed to heat or ultraviolet light, then crosslinking would occur between the double bonds.

The polymeric material may be a polyurethane foam formed from the mixture of isocyanates and polyols. Polyurethane foams are formed form the reactions of isocyanates and acids. As an example of such methylene diisocyanate reaction with polyvinyl acetic acid copolymerized with polyethylene oxide would cause the formation of a crosslinked polymer and the release of carbon dioxide, which would form the foaming agent.

The polymeric material may also be a latex material or a polymer formed from a free radical reaction with a secondary catalyst added after the polymer. The polymer may be altered by heat, light or laser energy to solidify.

The device may alternatively be formed from mixtures of methyl methacrylate 70% by weight, and butlymethacrylate 29% by weight and AIBN initiator, which would be hardened by exposure to either light, heat or laser energy.

The polymer may also be formed from polyisocyanates and amines or hydroxyl groups. Other more slowly crosslinking reagents such as aldehydes added in excess to proteins such as collagen could be used as well.

In its deliverable form, plug 12 would preferably be bathed or presoaked in an organic solution or aqueous solution of a specific pH or ionic concentration. This is because the mechanism of hardening in this case resides with the transition or replacement of one fluid for another. For instance, a solution of water and DMSO (dimethylsulfoxide) at a specific pH would keep the polymer soft and contracted. Once the fluid is replaced by a second fluid at a different pH probably near physiological pH, or in contact with blood, the polymer expands and hardens. There may be three phases to the phase change, governed by the fluid contacting the polymer: 1) soft and contracted; 2) soft and expanded; and 3) hard and expanded. This would be accomplished by a ternary system of fluid that modifies both pH and ionic strength or hydrophilicity, all of which would be delivered to the plug in-situ via the catheter.

Polymers that would alter their modulus through a change in pH include acid soluble collagen or poly-L-lysine which precipitates above a pH of 3.0. Polymers such as low molecular weight poly-L-lactic acid are soluble in DMSO and would precipitate on replacing the water miscible DMSO with water or saline solutions.

The delivery and placement of plug 12 in a septal defect is illustrated in FIGS. 4a and 4b, which depict placement of the plug and removal of delivery catheter 20,20'. Like FIG. 1, FIGS. 4a and 4b depict defects 6,6' of both atrial septal tissue 5 and ventricular septal tissue 5', respectively.

The route by which the cardiac defects are accessed via catheter are described as follows. An ASD or VSD may be accessed from the arterial circuit, as shown in FIG. 4a. The catheter/device is introduced into the arterial vascular system and guided up the descending thoracic and/or abdominal aorta. The device may then be advanced into the left ventricle (LV) 50 through the aortic outflow tract. Once in LV 50, the device may be deployed in VSD 6'. Alternatively, once in LV 50, the device may be directed up through mitral valve 54 and into the left atrium (LA) 56. When the device is in LA 56, it may be directed into ASD 6 and deployed. In FIG. 4a, plug 12 is shown already in place in ASD 6 with catheter/delivery means 20 in the process of being withdrawn. Plug 12' is shown being placed in VSD 6'. Plug 12' is delivered to the area of septal defect 6' by catheter 20' and inserted in place, centered in septal defect 6' as shown in FIG. 4a. Plug 12' may be either pulled or pushed out of catheter 20'. Upon expulsion from its delivery system, plug 12' will assume its preformed shape in a narrow center portion with enlarged ends. Plug 12 is shown in place closing off atrial septal defect 6, as corkscrew holder 24 and catheter delivery means 20 are being withdrawn.

Alternatively, an ASD or VSD may be accessed from the venous circuit, as shown in FIG. 4b. The catheter/device may be introduced into the venous system, advanced into Inferior Vena Cava (IVC) 62 or Superior Vera Cava (SVC) 64 and guided into the right atrium (RA) 60. The device may then be directed into ASD 6.

Alternatively, once in RA 60, the device may be advanced through tricuspid valve 66 into the right ventricle (RV) 58 and directed into VSD 6' and deployed. In FIG. 4b, plug 12 is shown being placed in ASD 6. Plug 12' is shown already in place in VSD 6' with catheter 20' in the process of being withdrawn. Plug 12 is delivered to the area of septal defect 6 by catheter 20 and inserted in place, centered in septal defect 6 as shown in FIG. 4b. Plug 12 may be either pulled or pushed out of catheter 20. Upon expulsion from its delivery system, plug 12 will assume its preformed shape in a narrow center portion with enlarged ends. Plug 12' is shown in place closing off ventricular septal defect 6', as corkscrew holder 24' and catheter delivery means 20' are being withdrawn.

After its placement in the area of defect 6, plug 12 is hardened in-situ. The polymeric material may be hardened by alterations in pH effected by infusion through catheter 20 of a solution of pH differing from the pH of the original solution. Alternatively, the material may be hardened by the addition of an organic solvent or through dilution. Hardening may also be effected by permeation into the pores of the polymeric material of a secondary material delivered by the catheter that would precipitate with a change in pH or by the addition of a secondary material in gel form or solution.

In an environment which includes blood, the plug 12 may be hardened through a cooperative effects of coagulation, precipitation or ionization. For example, the plug may comprise a gum or foam containing fibrinogen, which will crosslink once it comes into contact with thrombin in blood. Alternatively, thrombin may be pumped into the foam from the catheter.

Fibrinogen crosslinks through reaction of thrombin. A plug may be formed by pumping or allowing the meshwork or fabric or balloon forming the seal to the defect with the patient's own blood. The meshwork or balloon could also be filled with thrombin solution at the same time. This would cause the formation of a solid gel within the balloon. The presence of thrombin within the balloon does not preclude the presence of other molecules of collagen that form structural networks, nor does it preclude the presence of solutions such as DMSO or low pH solvents as previously described.

Further, since the blood is at physiological pH, the plug may contain or be comprised of high molecular weight acid soluble collagen. Once the collagen reaches a pH above about 4, it will precipitate. Chitosan, which is soluble in mixtures of polyethylene glycol (PEG), will precipitate as the PEG diffuses away from the surface of the plug. If the crosslinking mechanism depends on the ionic crosslinking by calcium ions, then chelating agents as EDTA could be infused to restrict such reaction until hardening is required. At the appropriate time, calcium ion containing solutions as calcium chloride, could be infused to trigger the crosslinking.

Within an acceptable period of time, on the order of one to fifteen minutes for example, the plug material will harden in place. The material may be permeated with biological components such as chemotactic or growth factors, that may be used to alter the reaction of the surrounding tissue.

An alternative embodiment of the device is shown in FIGS. 5–8, comprising a sleeve 112 of polymeric material which is placed over an expandable dumbbell-shaped (double lobed) balloon 124 located at the distal end 122 of catheter 120. Alternatively, sleeve 112 may be delivered on a perfusion catheter (not shown).

Polymeric material such as crosslinked collagen which is hardened by an increase in pH, or combinations of collagen and carbohydrates such as chitosan which swell upon hydration, or crosslinked collagen and carbohydrates which are first saturated in an organic solution such as DMSO or light oils to retard hydration until expansion may be used. The expandable material may simply be stretched beyond its yield point as with low density polyethylene or polypropylene to take the shape of the balloon.

The material may be hardened by heat or light energy if it contains crosslinkable moieties. Thus collagen, carbohydrates, polylactic or polyglycolic acid or combinations of these could be copolymerized with acrylic acid, or butadiene or other agents containing reactive double bonds. The homopolymer or copolymer may also contains more mobile low molecular weight polymers that could react with the side chains of the main polymer. After expansion into the appropriate shape, energy would be applied to crosslink and thus harden the material.

Figure 6:
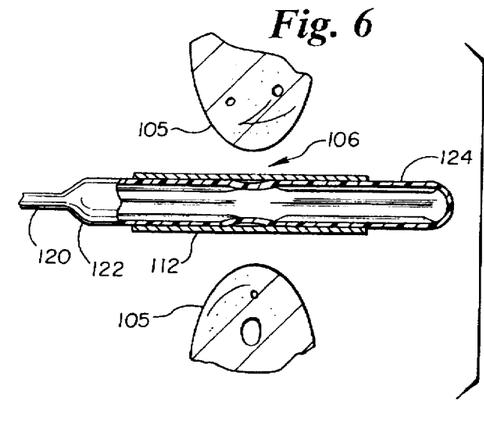
FIG. 6 is a fragmentary sectional view of the septal defect closure device of FIG. 5 in place in the area of septal defect prior to expansion of the sleeve and expansion balloon.

As shown in FIG. 6, sleeve 112 is delivered to the site of defect 106 by means of balloon 124. Balloon 124 is inflated after delivery, allowing sleeve 112 to contact the septal tissue 105, as is shown in FIG. 7. The polymeric material is hardened while balloon 124 is inflated giving shape to sleeve 112, thereby causing sleeve 112 to harden into a plug. After hardening of sleeve 112, balloon 124 is deflated and removed from the site of defect 106. The removal of balloon 124 leaves a small opening 126 through the center of the plug formed by sleeve 112, whose effect is negligible. FIG. 8 shows this embodiment in place in septal defect 106.

FIGS. 9–11 show a further alternative embodiment of the inventive septal defect closure device wherein plug 212 comprises an outer balloon 224 located at distal end 222 of catheter 220, into which polymeric material 214 is introduced through catheter 220. Polymeric material 214 is introduced into balloon 224, both polymeric filler 214 and balloon 224 being preferably made of bioabsorbable material.

Such biodegradable/bioabsorbable materials include collagen, carbohydrates, polyphosphazine and low molecular weight aliphatic polyesters as described above. Degradable materials that could be used for the balloon include polycaprolactone, and polyvalerolactone with copolymers of lactides. These polymers would impart to the balloon an ability to stretch to fill the defect. The defect filling balloon may be essentially noncompliant and could be comprised of thin fibers woven into an impermeable mesh or semipermeable mesh. Such fibers could be made of collagen, lactides, glycolides, or coweaves of such materials.

Balloon 224 is delivered to the site of the defect by catheter 220. Balloon 224 may be fully inflated with polymeric material 214 through balloon opening 226 or alternatively, partially inflated with polymeric material 214 and inflated with a solution or gel in place. Balloon opening 226 is visible in hardened plug 212, as shown in FIG. 11.

The balloon may be separated from the catheter by means of prestressed yield point, ball or spring friction detents, reversible threads, latches operated from the exterior of the patient, or the like.

Figure 12:
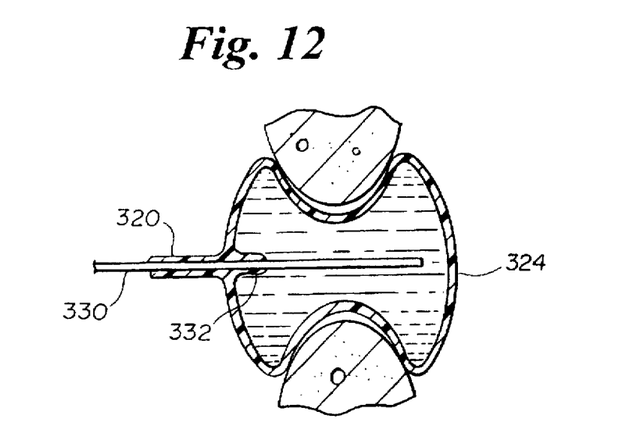
FIGS. 12 and 13 are fragmentary views showing an alternative embodiment of the septal defect closure device, the device comprising an expansion balloon with a one-way valve inflated with a liquid material at an elevated temperature which solidifies into a gel as it attains body temperature.
Figure 13:
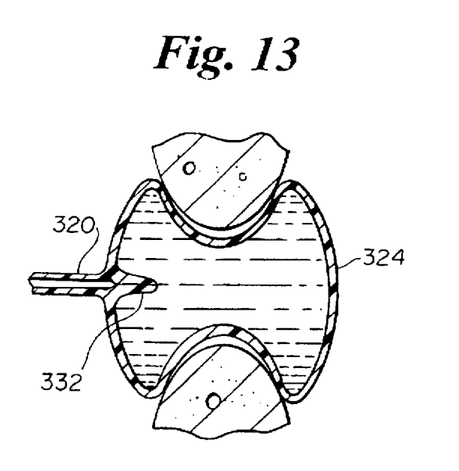

Referring to FIGS. 12 and 13, an alternative embodiment is shown. Balloon 324 is inflated via inner shaft 330 of catheter 320 with filling material 314, a liquid solution of materials which gel upon cooling. This filling material 314 may include biocompatible, biodegradable or bioabsorbable water soluble materials such as gelatin, collagen, albumin, agar or other such materials. Filling material 314 could also contain bioactive components which encourage the migration, growth or attachment of cells, such as collagen, albumin, growth factors (such as βFibroblastic Growth Factor), angiogenic factors, RGD adhesion sequences, or other factors or agents such as antibiotics that are commonly used for this purpose.

Specifically possible filling materials included combinations of diisocyanates and organic acids that liberate $CO_2$ upon mixing as methylenediphenyldiisocyanate (MDI) and acetic acid. This particular combination would form $CO_2$ but would not form a crosslinked solution. Other multi-ionic organic acids as citric acid could be used to form crosslinks. Also, if the acid containing molecules were polymers as 1-4 dicarboxylicbutylene a urethane crosslink would be formed while at the same time liberating $CO_2$ for foam formation. By variations in the number of acid groups and the distance apart the openness of the foam, the number of bubbles and the hardness or modulus of the filling material could be adjusted. In each case other crosslinking components could be added for stability while at the same time using acid components for gas evolution.

Other non-gas forming materials could be used for filling. One example is crosslinked microbeads of water swelling material as polyvinylpyrrolidone (PVP). Microbeads as these would swell to about ten times their original size and could be carried in within a stabilizing material. Collagen microbeads could be used for a similar purpose but with less swelling. Combinations of collagens, carbohydrates and PVP could be used as well.

The carrier or stabilizing material could be comprised of the isocyanates mentioned above or could be comprised of materials that form chemical bonds by free radical addition. In particular the acrylates and acrylamides could be injected in solution form and activated with heat or light in the presence of an initiator. The heat or light energy could be supplied on an optic fiber or heated probe positioned in the injection lumen. Combinations of swelling material as collagen or PVP microbeads and acrylates or diacrylates as neopentyldiacrylates could be used for the filling purposes.

Following removal of the outer protective sheath of catheter 320, balloon 324 is inflated in place with filling material 314 containing bioactive factors at a slightly elevated temperature, between about 38°-80° C., such that filling material 314 is in solution. Following inflation, filling material 314 will harden upon cooling to body temperature, and inner shaft 330 is removed. Balloon 324 may be made of biodegradable or non-biodegradable biocompatible polymeric material, as disclosed hereinabove. Balloon 324, like filling material 314, may include growth factors and other mitogenic agents.

Balloon 324 may include a one-way valve 332 located at the point where inner shaft 330 of catheter 320 enters balloon 324. After inflation, inner shaft 330 would be removed and valve 332 would prevent filling material 314 from leaking from balloon 324 until filling material 314 solidifies. This would allow removal of the outer shaft of catheter 320 while filling material 314 is still in solution.

The septal defect plug of the present invention may be made of biodegradable, bioabsorbable material such that tissue ingrowth can occur over a period of time. These materials include those commonly used for sutures, skin grafting or vessel repair, as such materials will permit tissue ingrowth. Thus collagens, such carbohydrates as chondoitin sulfate, lactides, glycolides and the like may also be employed.

Figure 14:
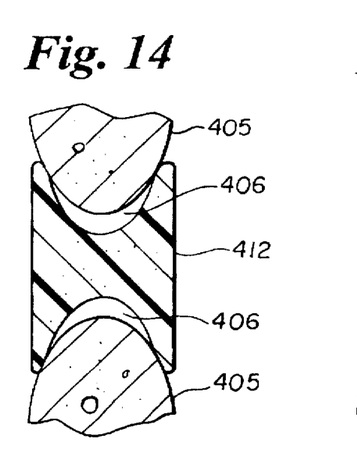
FIGS. 14, 15 and 16 are sectional views showing an alternative embodiment of the invention which is bioabsorbable.
Figure 15:
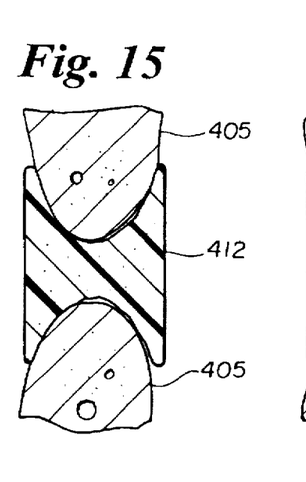
Figure 16:
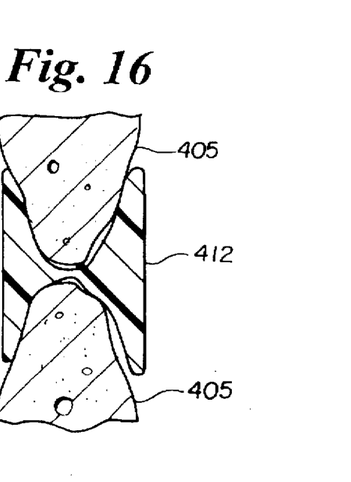

FIGS. 14-16 show septal defect plug 412 according to the present invention in place in septal defect 406, contacting septal tissue 405 on both sides. FIGS. 14 and 16 show the bioabsorption of plug 412 and the generation of septal tissue 405, thereby filling septal defect 406. Impregnated growth factors, collagen gel or fibrils, mitogenic factors or other determinants which can improve tissue growth may be added to enhance regeneration of the septal tissue.

Determinants that could improve or accelerate growth include collagen type I, type III or type IV, collagen type IV with laminin, platelet growth factor, fibronectin, vitronectin, glycoprotein IIb, IIIa, and the like.

The septal defect closure device of the present invention has the general properties of being suitable for filling a defect. The shape of the containment system may be a dumbbell for some septal defects, but may also take other shapes and may even take the shape of a defect itself when the defect is not uniform in shape or if the system is used for a vessel such as the ductus. In this case the containment system may be deformable or flexible. The material of the containment system may be formed of a solid film or of a woven mesh. The containment may also be provided by the surface of the foam itself.

Figures 17, 18, 19, 20:
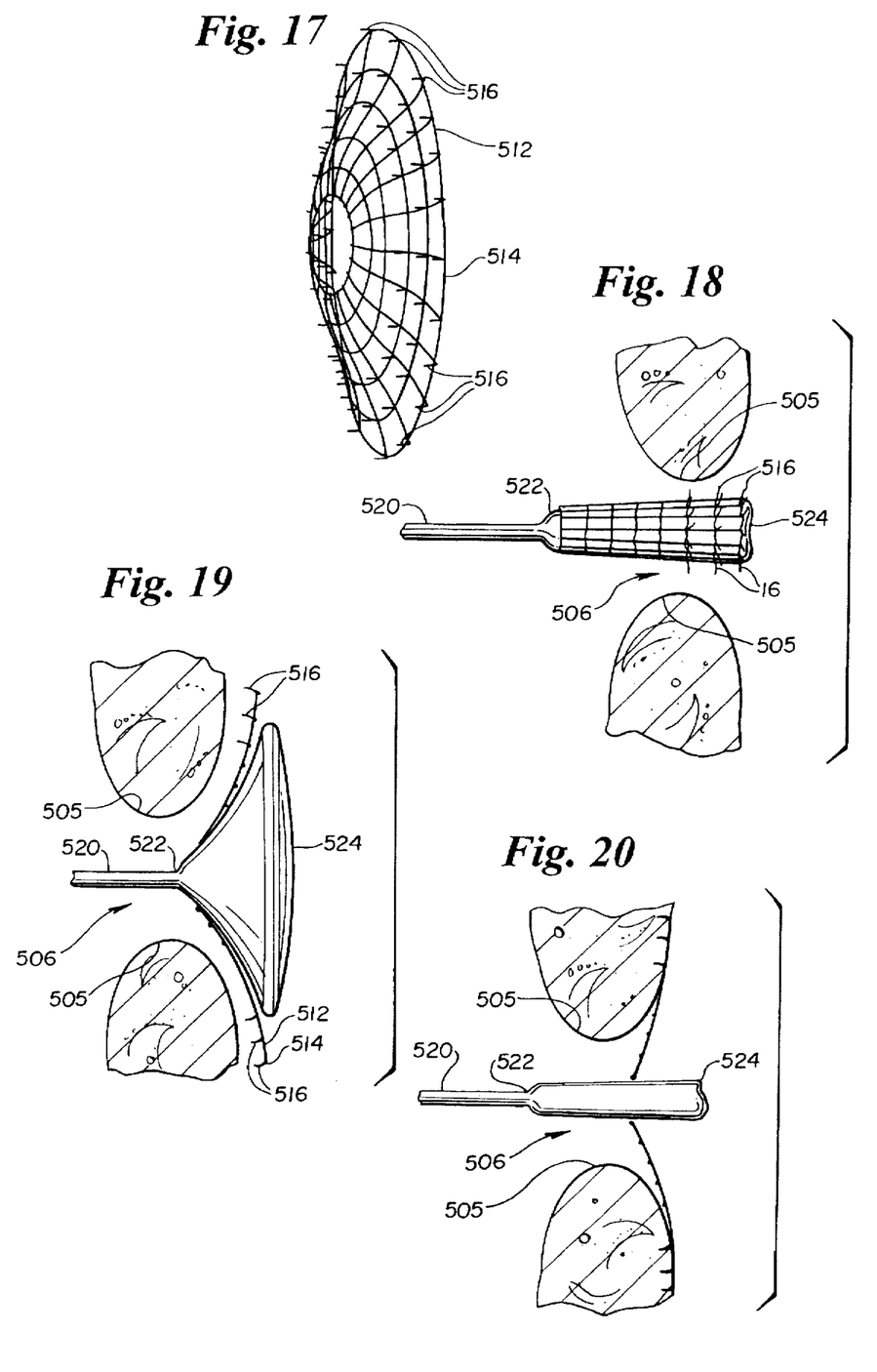
FIG. 17 is a perspective view of an alternative embodiment of the septal defect closure device, the device comprising a biocompatible mesh sleeve and an expansion balloon.
FIG. 18 is a fragmentary sectional view of the septal defect closure device of FIG. 17 in place in the area of septal defect prior to expansion of the sleeve expansion balloon.
FIG. 19 is a fragmentary sectional view thereof showing the expansion balloon and the expanded mesh closure sleeve in place in the septal defect.
FIG. 20 is a fragmentary sectional view showing the expanded mesh closure sleeve in place in the septal defect as the expansion balloon is being removed.

A further additional embodiment is shown at FIGS. 17-22. In this embodiment, sleeve 512 comprises a mesh. As shown in FIG. 17, mesh sleeve 512 has a plurality of attachment means 516 (taking form of hooks) located thereon. Alternatively, attachment means may merely be located at fewer selected locations of expanded sleeve 512. The hooks may be comprised of high modulus material such as poly-1-glycolide, crosslinked collagen, dacron, high density polyethylene fibers, chitin, or metals such as stainless steel.

Mesh sleeve 512 is placed over an expandable balloon prior to delivery. FIG. 18 shows sleeve 512 placed over expandable balloon 524 located at the distal end 522 of catheter 520, at the site of defect 506 prior to expansion of balloon 524. Although the balloon may be of any suitable shape, a bell-shaped balloon is shown. Alternatively, mesh sleeve 512 may be delivered on a perfusion catheter.

As shown in FIG. 19, balloon 524 is inflated after delivery, allowing mesh sleeve 512 to contact the septal tissue 505, as is shown in FIG. 20. Mesh sleeve 512 is hardened while balloon 524 is inflated giving shape to sleeve 512, which is attached to the tissue by at least two attachment means 516 located at periphery 514 of mesh 512, or by chemical means. Such chemical means of attaching the mesh to the septal wall include the positioning of micro or macro capsules (1 micron to 1 millimeter in diameter) of butylcyanoacrylate on the tissue mating surface. The microcapsules would burst when pressed against the surface or could be scored with an indentation to crack or squeeze open when the mesh is stretched or pressed. Synthetic muscle adhesive proteins or diisocyantes could be used in place of the cyanoacrylates.

As shown in the figures, multiple attachment means may be utilized. Referring to FIG. 20, after deployment of sleeve 512, balloon 524 is deflated and removed from the site of defect 506. The removal of balloon 524 leaves mesh 512 in place, spanning defect site 506.

Figure 21:
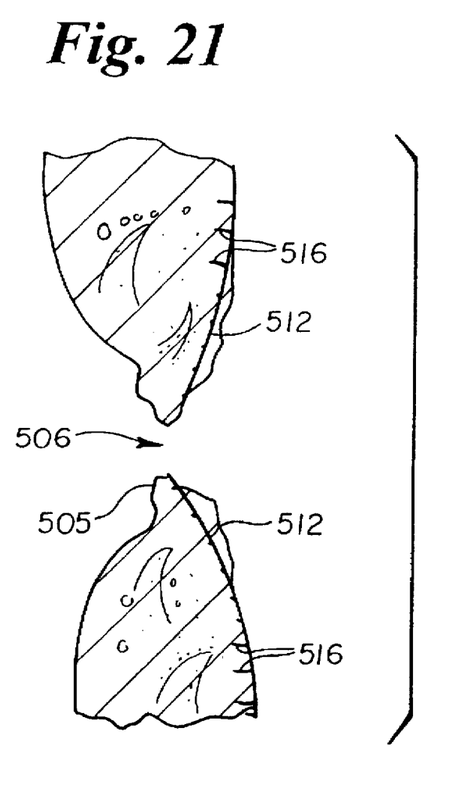
FIGS. 21 and 22 are fragmentary sectional views showing the filling in of the defect around the mesh closure sleeve.
Figure 22:
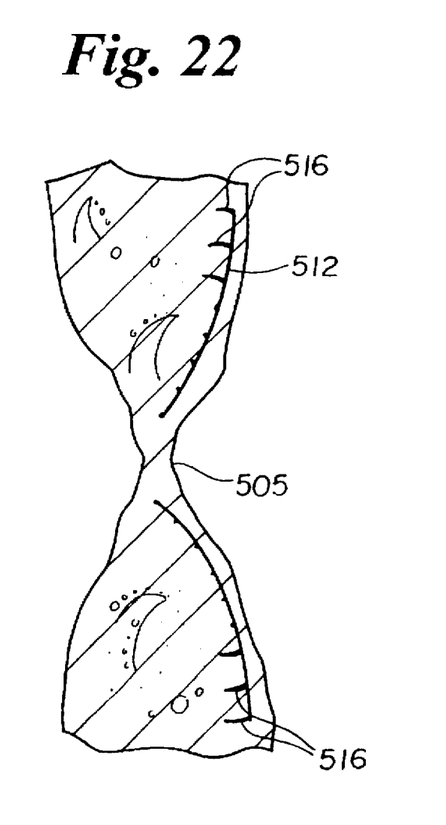

After mesh 512 is placed over the defect, blood will initially be able to pass therethrough. With time, however, cells induced to grow onto the meshwork would provide a more complete closure of the defect. FIGS. 21 and 22 show the ingrowth of tissue causing the closure of the defect.

The mesh would initially be attached to the tissue by physical attachment means 516, or by chemical means. This would provide relatively weak attachment compared to that which will occur after tissue overgrowth. The tissue overgrowth provides not only a strengthening of the attachment site but also the deposition of cellular and fibrillar material across the body of the meshwork which will eventually provide the blockage to blood flow.

The meshwork itself could be comprised of PET, or PTFE, or other long lasting material or it could be comprised of fibers of a degrading material as caprolactone or polylactic acid or a combination of these. Such a degrading material could be composed of fibers of polylactic acid, polyglycolic acid, collagen, chondroitin sulfate, or coweaving of any of these materials. If a degradable material were used, the meshwork would be comprised of several layers of a knit or weave such that a wall of substantial thickness, 3 to 5 mm, would be generated by cellular and fibrillar overgrowth and that this wall of tissue would itself be capable of resisting the pressure difference between the opposing chambers.

The molecular components that would induce cellular overgrowth would be comprised of the materials known as CAMs or cellular adhesive molecules. Among the class of biological materials are fibronectin and vitronectin. Generally, films or substrates containing collagen and or fibrin will also suffice. These biological materials may, if in fibrous form, be woven into the meshwork as a member of a composite fiber. They may also be deposited onto the surface of the fibers by one or more of several chemical means. Covalent bonds may be formed between the surface of RF plasma activated PET or PTFE and aliphatic ligands that themselves attach to the biologically active molecule or to segments thereof.

RF plasma techniques produce reactive species including free radicals on most materials. These reactive species include hydroxylated, chlorinated or aminated surfaces. These chemical components may be reacted in turn with any one of a number of chemical ligands which would subsequently react with tissue.

While this invention may be embodied in many different forms, there are described in detail herein specific preferred embodiments of the invention. This description is an exemplification of the principles of the invention and is not intended to limit the invention to the particular embodiments illustrated.

The practice of the present invention achieves several objectives and advantages. Currently, there are no percutaneous devices available to cure a septal defect or the like. The device and method of the present invention provides an advantage over surgery in that the cost of the procedure is substantially less, the risk of infection is less, the hospital residency time is less and there is no physically deforming scar.

In comparison with umbrella type devices or simple balloon, the septal defect closure device of the present invention has the advantage of adhering to tissue immediately. It can promote healing at a rapid rate. There is less risk of embolism if the device fills the defect rather than sitting on the surface of the tissue surrounding the defect since that tissue can be quite filamentous.

In regard to filling the ductus, which can be approached using a coil, coils cannot be used in large ductus (greater than about 0.5 cm) and the ductus must be funnel like in shape so that the coil does not fall through. A material that conforms to the wall of the ductus and adheres to it will stay in place.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An apparatus for permanently closing off a septal defect, the apparatus comprising:
   a. a plug comprising a polymeric material which is cured or hardened in situ, said plug being unitary in construction and having a first end and a second end, the plug being directly introduced into the area of a septal defect;
   b. a catheter having a first end and a second end, the catheter being adapted to carry and release the plug;
   c. means for releasably securing the plug to the catheter; whereby the plug is delivered to the defect area by the catheter, placed in the septal defect, released from the catheter and cured or hardened in situ, whereby the hardened plug remains, plugging the defect.

2. The apparatus of claim 1 wherein the plug is made of a bioabsorbable polymeric material that reacts to heat, light, alterations in pH or chemical reactants.

3. The apparatus of claim 2 wherein the polymeric material includes growth factors and other mitogenic agents.

4. The apparatus of claim 1 wherein the catheter includes a balloon at its second end, said balloon being unitary in construction and having a specific conformation which is adapted to fit securely into the defect upon being positioned therein and substantially close it, and the plug comprises a sleeve which encases the balloon.

5. The apparatus of claim 4 wherein the plug is released from the catheter by deflation of the balloon.

6. The apparatus of claim 1 wherein the plug comprises a polymeric material which is relatively soft and compliant in a first state, the plug being of a specific configuration which is adapted to fit securely into the defect upon being positioned therein and substantially close it, said polymeric material being capable of being cured and changed to a hardened second state in-situ, whereby the defect is permanently closed by said plug of cured polymeric material.

7. An apparatus for closing off a septal defect, the apparatus comprising:
   a. a plug having a first end and a second end, the plug being directly introduced into the area of a septal defect; and
   b. a catheter having a first end and a second end, the catheter being adapted to carry and release the plug, said catheter including a corkscrew at its second end whereby the plug is releasably secured thereto;

whereby the plug is delivered to the defect area by the catheter, placed in the septal defect and released from the catheter so it remains, plugging the defect.

8. An apparatus for closing off a septal defect, the apparatus comprising:
   a. a plug having a first end and a second end, the plug being directly introduced into the area of a septal defect;
   b. a catheter having a first end and a second end, the catheter being adapted to carry and release the plug, said catheter further comprising a threaded protrusion at its second end adapted to mate with a threaded bore located at the first end of the plug, whereby the plug is releasably secured to the catheter;
whereby the plug is delivered to the defect area by the catheter, placed in the septal defect and released from the catheter so it remains, plugging the defect.

9. An apparatus for closing off a septal defect, the apparatus comprising:
   a. a plug having a first end and a second end, said plug comprising a balloon filled with polymeric foam, the plug being directly introduced into the area of a septal defect;
   b. a catheter having a first end and a second end, the catheter being adapted to carry and release the plug;
   c. means for releasably securing the plug to the catheter; whereby the plug is delivered to the defect area by the catheter, placed in the septal defect and released from the catheter so it remains, plugging the defect.

10. The apparatus of claim 9 wherein the catheter includes a fluid delivery lumen by means of which the polymeric foam is hardened after delivery to the area of defect.

11. The apparatus of claim 9 wherein the balloon is made of bioabsorbable material.

12. The apparatus of claim 9 wherein the balloon and polymeric material include growth factors and other mitogenic agents.

13. An apparatus for closing off a septal defect, the apparatus comprising:
   a. a plug having a first end and a second end, the plug being directly introduced into the area of a septal defect, said plug further comprising:
      i. a dual-lobed balloon made of polymeric material; and
      ii. a liquid solution which is introduced into the balloon at an elevated temperature and hardens into a gel upon cooling in-situ to body temperature;
   b. a catheter having a first end and a second end, the catheter being adapted to carry and release the plug;
   c. means for releasably securing the plug to the catheter; whereby the plug is delivered to the defect area by the catheter, placed in the septal defect and released from the catheter so it remains, plugging the defect.

14. The apparatus of claim 13 wherein the liquid solution introduced into the balloon comprises a water soluble composition selected from the group consisting of gelatin, collagen, albumin, agar and mixtures thereof.

15. The apparatus of claim 14 wherein the composition further includes bioactive components selected from the group consisting of collagen, albumin, βFibroblastic Growth Factor, angiogenic factors, RGD adhesion sequences, antibiotics and mixtures thereof.

16. The apparatus of claim 3 wherein the balloon is made of biodegradable polymeric material.

17. The apparatus of claim 13 wherein the balloon is made of non-biodegradable, biocompatible polymeric material.

18. The apparatus of claim 13 wherein the balloon and liquid solution include growth factors and other mitogenic agents.

19. An apparatus for closing off a septal defect, the apparatus comprising:
   a. a catheter having a first end and a second end, the catheter including at its second end a balloon having a specific conformation adapted to fit securely into the defect upon being positioned therein and substantially close it,
   b. a plug having a first end and a second end, the plug comprising a sleeve which encases the balloon, said catheter being adapted to carry and release the plug, said plug being directly introduced into the area of a septal defect, said sleeve further being made of a deformable polymeric material, said sleeve being permanently deformed by the balloon within the defect in the shape of a plug, leaving the defect substantially plugged after deflation and removal of the balloon;
whereby the plug is delivered to the defect area by the catheter, placed in the septal defect and released from the catheter so it remains, plugging the defect.

20. The apparatus of claim 19 wherein the balloon is dumbbell shaped.

21. The apparatus of claim 19 wherein the polymeric material includes growth factors and other mitogenic agents.

22. The apparatus of claim 19 wherein the polymeric material is made of a bioabsorbable material tilt reacts to heat, light, alterations in pH, or organic solvents.

23. The apparatus of claim 19 wherein the polymeric material reacts to electromagnetic energy, infrared light, visible light or ultraviolet light.

24. An apparatus for closing off a septal defect, the apparatus comprising:
   a. a catheter having a first end and a second end, said catheter including at its second end a balloon having a specific conformation adapted to fit securely into the defect upon being positioned therein and substantially close it;
   b. a plug having a first end and a second end, the plug being directly introduced into the area of a septal defect, the catheter being adapted to carry and release the plug, the plug comprising a deformable sleeve-like mesh of a bioabsorbable polymeric material, the mesh contacting the surrounding surface area of the septal defect when the balloon is inserted therein and inflated, said sleeve-like mesh encasing the balloon for delivery thereof, whereby the sleeve-like mesh may be delivered to the defect and permanently deployed by the balloon, leaving a mesh across the defect after deflation and removal of the balloon.

25. The apparatus of claim 24 wherein the balloon is bell shaped.

26. The apparatus of claim 24 wherein the polymeric material includes growth factors and other mitogenic agents.

27. The apparatus of claim 24 wherein the sleeve-like mesh is delivered to an area of defect through a catheter and secured to the area surrounding the detect by physical or chemical means.

28. The apparatus of claim 24 wherein the polymeric material is made of a bioabsorbable material that reacts to head, light, alterations in pH, or organic solvents.

29. The apparatus of claim 24 wherein the mesh is made of PET.

30. The apparatus of claim 24 wherein the mesh is made of PTFE.

31. The apparatus of claim 24 wherein the mesh is comprised of a material selected from the group consisting of caprolactone, polylactic acid and mixtures thereof.

32. The apparatus of claim 24 wherein the mesh further includes a bioactive material selected from the group consisting or fibronectin, vitronectin, collagen, fibrin and mixtures thereof.

33. The apparatus of claim 32 wherein the bioactive material is in fibrous form and is woven into the meshwork as a member of a composite fiber.

34. The apparatus of claim 32 wherein the bioactive material is deposited onto the surface of the fibers by chemical means.

35. An apparatus for closing off a septal defect, the apparatus comprising:
   a. a plug having a first end and a second end, said plug comprising a compressible polymeric foam made of a bioabsorbable material that reacts to heat, light, alterations in pH or chemical reactants, the plug being directly introduced into the area of a septal defect;
   b. a catheter having a first end and a second end, the catheter being adapted to carry and release the plug;
   c. means for releasably securing the plug to the catheter; whereby the plug is delivered to the defect area by the catheter, placed in the septal defect and released from the catheter so it remains, plugging the defect.

36. The apparatus of claim 35 wherein the polymeric material includes growth factors and other mitogenic agents.

37. The apparatus of claim 36 wherein the polymeric foam is presoaked in an organic or aqueous solution of a specific pH to retain its compressibility.

38. The apparatus of claim 31 wherein the catheter includes a fluid delivering lumen by means of which the polymeric foam is hardened after delivery to the area of defect by infusion through the catheter of a solution of a different pH than the solution in which the apparatus was presoaked.

39. The apparatus of claim 37 wherein the polymeric material is presoaked in an organic solution, and the catheter includes a fluid delivering lumen by means of which the polymeric foam is hardened after delivery to the area of defect by the removal of the organic solution by dilution.

40. The apparatus of claim 35 wherein the polymeric foam is hardened by the permeation therein or a second material which precipitates with a change in pH.

41. The apparatus of claim 40 wherein the second material is a gel.

42. The apparatus of claim 40 wherein the second material is a solution.

43. The apparatus of claim 40 wherein the alteration of the first state is effected in the presence of blood through a cooperative effect of coagulation, precipitation or ionization.

44. An apparatus for closing off a septal defect, the apparatus comprising:
   a. a plug having a first end and a second end, said plug being made of a bioabsorbable polymeric material that reacts to light and is hardened by photopolymerization, the plug being directly introduced into the area of a septal defect;
   b. a catheter having a first end and a second end, the catheter being adapted to carry and release the plug;
   c. means for releasably securing the plug to the catheter; whereby the plug is delivered to the defect area by the catheter, placed in the septal defect and released from the catheter so it remains, plugging the defect.

45. An apparatus for permanently closing off a septal defect, the apparatus comprising:
   a. a plug comprising a polymeric material which is cured or hardened in situ, said plug being unitary in construction and having a first end and a second end, the plug being directly introduced into the area of a septal defect;
   b. a catheter having a first end and a second end, the catheter being adapted to carry and release the plug;
   c. means for releasably securing the plug to the catheter; whereby the plug is delivered to the defect area by the catheter, placed in the septal defect, released from the catheter and cured or hardened in situ, whereby the hardened plug remains, plugging the defect.

46. The apparatus of claim 45 wherein the catheter includes a balloon at its second end, said balloon being unitary in construction and having a specific conformation which is adapted to fit securely into the defect upon being positioned therein and substantially close it, and the plug comprises a sleeve which encases the balloon.

* * * * *

UNITED STATES PATENT AND TRADEMARK OFFICE
CERTIFICATE OF CORRECTION

PATENT NO. : 5,634,936

DATED : June 3, 1997

INVENTOR(S) : Linden et al.

It is certified that error appears in the above-identified patent and that said Letters Patent is hereby corrected as shown below:

at column 13, line 61, delete "3" and insert therefor -- 13 --;
at column 14, line 24, delete "tilt" and insert therefor -- that --;
at column 15, line 25, delete "31" and insert therefor -- 37 --, and
at column 15, line 33, delete "Iumen" and insert therefor -- lumen --.

Signed and Sealed this

Sixteenth Day of September, 1997

Attest:

BRUCE LEHMAN

*Attesting Officer*  *Commissioner of Patents and Trademarks*